US012257378B2

(12) United States Patent
Case

(10) Patent No.: US 12,257,378 B2
(45) Date of Patent: Mar. 25, 2025

(54) DYNAMIC ADJUSTMENT OF ALGORITHMS FOR SEPARATION AND COLLECTION OF BLOOD COMPONENTS

(71) Applicant: Fenwal, Inc., Lake Zurich, IL (US)

(72) Inventor: Brian C. Case, Lake Villa, IL (US)

(73) Assignee: Fenwal, Inc., Lake Zurich, IL (US)

( * ) Notice: Subject to any disclaimer, the term of this patent is extended or adjusted under 35 U.S.C. 154(b) by 0 days.

(21) Appl. No.: 18/599,377

(22) Filed: Mar. 8, 2024

(65) Prior Publication Data

US 2024/0238499 A1   Jul. 18, 2024

Related U.S. Application Data

(63) Continuation of application No. 17/019,397, filed on Sep. 14, 2020, now Pat. No. 11,957,828.

(60) Provisional application No. 62/900,957, filed on Sep. 16, 2019.

(51) Int. Cl.
| | |
|---|---|
| *A61M 1/36* | (2006.01) |
| *B01D 21/26* | (2006.01) |
| *B01D 21/30* | (2006.01) |
| *B01D 63/16* | (2006.01) |

(52) U.S. Cl.
CPC ......... *A61M 1/3696* (2014.02); *B01D 21/262* (2013.01); *B01D 21/30* (2013.01); *B01D 63/16* (2013.01)

(58) Field of Classification Search
None
See application file for complete search history.

(56) References Cited

U.S. PATENT DOCUMENTS

| | | | |
|---|---|---|---|
| 5,194,145 | A | 3/1993 | Schoendorfer |
| 5,632,893 | A | 5/1997 | Brown et al. |
| 5,637,082 | A | 6/1997 | Pages et al. |
| 5,868,696 | A | 2/1999 | Giesler et al. |

(Continued)

FOREIGN PATENT DOCUMENTS

| | | |
|---|---|---|
| EP | 1946784 B1 | 10/2012 |
| WO | WO 2002/069793 A2 | 9/2002 |

(Continued)

OTHER PUBLICATIONS

Extended European Search Report, dated Feb. 8, 2021, for application No. EP20195921.0-1113.

(Continued)

*Primary Examiner* — Bradley R Spies
*Assistant Examiner* — Jeannie McDermott
(74) *Attorney, Agent, or Firm* — Cook Alex Ltd.

(57) ABSTRACT

Blood is conveyed from a source into a separator, which separates at least one target blood component from the blood. The target blood component is then conveyed out of the separator, with the procedure continuing until an initial target amount of blood to be processed has been conveyed from the source into the separator and the target blood component separated from the initial target amount of blood to be processed has been conveyed out of the separator as an actual yield of the target blood component. An adjusted target amount of blood to be processed is then determined based at least in part on the difference between a target yield of the target blood component and the actual yield. The initial target amount of blood to be processed is then replaced with the adjusted target amount of blood to be processed when next executing the procedure.

20 Claims, 2 Drawing Sheets

(56) References Cited

U.S. PATENT DOCUMENTS

| | | |
|---|---|---|
| 6,251,284 B1 | 6/2001 | Bischof et al. |
| 6,312,607 B1 | 11/2001 | Brown et al. |
| 6,419,822 B2 | 7/2002 | Muller et al. |
| 6,471,855 B1 | 10/2002 | Odak et al. |
| 6,579,219 B2 | 6/2003 | Dolecek et al. |
| 6,582,386 B2 | 6/2003 | Min et al. |
| 6,629,919 B2 | 10/2003 | Egozy et al. |
| 6,706,008 B2 | 3/2004 | Vishnoi et al. |
| 6,770,883 B2 | 8/2004 | McNeal et al. |
| 6,808,503 B2 | 10/2004 | Farrell et al. |
| 6,866,826 B2 | 3/2005 | Moore et al. |
| 6,869,411 B2 | 3/2005 | Langley et al. |
| 6,884,228 B2 | 4/2005 | Brown et al. |
| 7,011,761 B2 | 3/2006 | Muller |
| 7,041,076 B1 | 5/2006 | Westberg et al. |
| 7,049,622 B1 | 5/2006 | Weiss |
| 7,081,082 B2 | 7/2006 | Scholz et al. |
| 7,150,834 B2 | 12/2006 | Mueth et al. |
| 7,186,230 B2 | 3/2007 | Briggs et al. |
| 7,186,231 B2 | 3/2007 | Takagi et al. |
| 7,211,037 B2 | 5/2007 | Briggs et al. |
| 7,294,513 B2 | 11/2007 | Wyatt |
| 7,347,948 B2 | 3/2008 | Dolecek et al. |
| 7,354,515 B2 | 4/2008 | Coull et al. |
| 7,381,291 B2 | 6/2008 | Tobe et al. |
| 7,422,693 B2 | 9/2008 | Carter et al. |
| 7,485,084 B2 | 2/2009 | Borgstrom et al. |
| 7,563,376 B2 | 7/2009 | Oishi |
| 7,648,639 B2 | 1/2010 | Holmes et al. |
| 7,708,710 B2 | 5/2010 | Min et al. |
| 7,806,845 B2 | 10/2010 | Arm et al. |
| 7,906,771 B2 | 3/2011 | Carter et al. |
| 7,951,059 B2 | 5/2011 | Sweat |
| 8,057,377 B2 | 11/2011 | Holmes et al. |
| 8,075,468 B2 | 12/2011 | Min et al. |
| 8,163,276 B2 | 4/2012 | Hedrick et al. |
| 8,287,742 B2 | 10/2012 | Holmes |
| 8,317,672 B2 | 11/2012 | Nash et al. |
| 8,337,379 B2 | 12/2012 | Fletcher et al. |
| 8,535,210 B2 | 9/2013 | Kolenbrander et al. |
| 8,545,427 B2 | 10/2013 | Holmer et al. |
| 8,556,793 B2 | 10/2013 | Foley et al. |
| 8,628,489 B2 | 1/2014 | Pages et al. |
| 8,758,211 B2 | 6/2014 | Nash et al. |
| 8,870,804 B2 | 10/2014 | Jonsson |
| 8,974,362 B2 | 3/2015 | Nash et al. |
| 9,011,687 B2 | 4/2015 | Swift et al. |
| 9,156,039 B2 | 10/2015 | Holmes et al. |
| 9,302,042 B2 | 4/2016 | Pages |
| 9,302,276 B2 | 4/2016 | Pesetsky et al. |
| 9,370,615 B2 | 6/2016 | Ragusa et al. |
| 9,399,182 B2 | 7/2016 | Pesetsky et al. |
| 9,550,016 B2 | 1/2017 | Gifford |
| 9,610,590 B2 | 4/2017 | Hamandi |
| 9,789,235 B2 | 10/2017 | Gifford et al. |
| 10,086,128 B2 | 10/2018 | Kyle et al. |
| 10,166,322 B2 | 1/2019 | Sweat et al. |
| 10,238,787 B2 | 3/2019 | Takuwa |
| 10,293,097 B2 | 5/2019 | Murphy et al. |
| 10,399,881 B2 | 9/2019 | Donais et al. |
| 10,413,652 B2 | 9/2019 | Foley et al. |
| 10,493,467 B2 | 12/2019 | Lundquist et al. |
| 10,518,007 B2 | 12/2019 | Kimura |
| 10,561,783 B2 | 2/2020 | Hamandi et al. |
| 2002/0046975 A1 | 4/2002 | Langley et al. |
| 2002/0128583 A1 | 9/2002 | Min et al. |
| 2004/0195190 A1 | 10/2004 | Min et al. |
| 2005/0049539 A1 | 3/2005 | O'Hara, Jr. et al. |
| 2009/0215602 A1 | 8/2009 | Min et al. |
| 2011/0003675 A1 | 1/2011 | Dolecek |
| 2011/0294641 A1 | 12/2011 | Dolecek et al. |
| 2012/0010062 A1 | 1/2012 | Fletcher et al. |
| 2014/0378292 A1 | 12/2014 | Igarashi |
| 2015/0068959 A1 | 3/2015 | Zheng |
| 2015/0104824 A1 | 4/2015 | Walker |
| 2015/0218517 A1 | 8/2015 | Kusters et al. |
| 2015/0367063 A1 | 12/2015 | Kimura |
| 2016/0166755 A1 | 6/2016 | Golarits et al. |
| 2016/0175509 A1 | 6/2016 | Planas et al. |
| 2017/0153431 A1 | 6/2017 | Nguyen et al. |
| 2017/0354770 A1 | 12/2017 | Radwanski et al. |
| 2018/0043374 A1 | 2/2018 | Meinig et al. |
| 2018/0164141 A1 | 6/2018 | Bordignon et al. |
| 2018/0185772 A1 | 7/2018 | Karhiniemi et al. |
| 2019/0003873 A1 | 1/2019 | Araujo et al. |
| 2019/0030545 A1 | 1/2019 | Hamada et al. |
| 2019/0083696 A1 | 3/2019 | Igarashi |

FOREIGN PATENT DOCUMENTS

| | | |
|---|---|---|
| WO | WO2012/091720 A1 | 7/2012 |
| WO | WO 2012/125457 A1 | 9/2012 |
| WO | WO 2013/043433 A2 | 3/2013 |
| WO | WO 2014/039091 A1 | 3/2014 |
| WO | WO 2018/053217 A1 | 3/2018 |
| WO | WO2018/154115 A2 | 8/2018 |
| WO | WO2019/047498 A1 | 3/2019 |
| WO | WO2019/165478 A1 | 8/2019 |
| WO | WO2020/002059 A1 | 1/2020 |
| WO | WO 2020/055958 A1 | 3/2020 |

OTHER PUBLICATIONS

Extended European Search Report, dated Apr. 25, 2022, for application No. EP21214264.0-1113.

A. Shokry, et.al, Dynamic Optimization of Batch Processes under Uncertainty via Meta-MultiParametric Approach, Computer Aided Chemical Engineering, vol. 40, 2017, pp. 2215-2220, ISSN 1570-7946, ISBN 97804446399653, https://doi.org/10.1016/B978-0-444-63965-3.50371-8. (Year: 2017).

B. Srinivasan, et. al, Dynamic optimization of batch processes: I. Characterization of the nominal solution, Computers & Chemical Engineering, vol. 27, Issue 1, 2003, pp. 1-26, ISSN 0098-1354, https://doi.org/10.1016/S0098-1354(02)00116-3. (Year: 2003).

Kai Liu, et. al, A survey of run-to-run control for batch processes, ISA Transactions, vol. 83, pp. 107-125, ISSN 0019-0578, https://doi.org/10.1016/j.isatra.2018.09.005. (Year: 2018).

B. Srinivasan, et. al, Dynamic optimization of batch processes: II. Role of mesaurements in handling uncertainty, Computers & Chemical Engineering, vol. 27, Issue 1, 2003, pp. 27-44, ISSN 0098-1354, https://doi.org/10.1016//S0098-1354(02)00117-5. (Year: 2003).

Y. Wang, et. al, Survey on iterative learing control, repetitive control, and run-to-run control, Journal of Process Control, vol. 19, Issue 10, 2009, pp. 1589-1600, ISSN 0959 1524, https://doi.org/10.org/10.1016/j.jprocont.2009.09.006. (Year: 2009).

DYNAMIC ADJUSTMENT OF ALGORITHMS FOR SEPARATION AND COLLECTION OF BLOOD COMPONENTS

CROSS-REFERENCE TO RELATED APPLICATIONS

This application is a continuation of U.S. patent application Ser. No. 17/019,397, filed Sep. 14, 2020, which claims the benefit of and priority of U.S. Provisional Patent Application Ser. No. 62/900,957, filed Sep. 16, 2019, the contents of which are incorporated by reference herein.

BACKGROUND

Field of the Disclosure

The invention relates to separation and collection of blood components. More particularly, the invention relates to dynamically adjusting algorithms that are employed during separation and collection of blood components.

Description of Related Art

Various blood processing systems now make it possible to collect particular blood constituents, instead of whole blood, from a blood source. Typically, in such systems, whole blood is drawn from a blood source, the particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

According to one approach, whole blood may be separated into its constituents through centrifugation. This requires that the whole blood be passed through a centrifuge after it is withdrawn from, and before any constituent thereof is returned to, the blood source. To reduce contamination and possible infection (if the blood source is a human donor or patient), the blood is preferably processed within a sealed, sterile fluid flow circuit during the centrifugation process. The operator installs a fresh, sterile disposable flow circuit in the centrifuge before processing and removes and discards it afterwards. Typical disposable flow circuits are sealed and sterile, and include a separation chamber portion, which is mounted in cooperation on a durable, reusable assembly containing the hardware (centrifuge, drive system, pumps, valve actuators, programmable controller, and the like) that rotates the separation chamber and controls flow through the fluid circuit. The separation chamber may be formed of a generally rigid material (e.g., molded plastic), in which case the chamber itself defines a flow path or channel in which blood is separated into two or more components, or a more flexible material (e.g., in the form of a belt or annulus), which relies upon the system hardware to support the chamber and define the shape of the chamber as blood flows through it.

With a disposable circuit loaded onto the centrifuge (or just prior to or during loading) the operator typically enters, for example, by means of a touch screen or other user interface system, a particular processing protocol to be executed by the system (e.g., a procedure wherein platelets are separated from whole blood and collected) and other parameters (e.g., the weight of the blood source, the desired volume of separated blood component to be collected, etc.). When the system has been programmed, the operator fluidly connects the source to the circuit and the system carries out the procedure, under the supervision of the operator.

The centrifuge rotates the separation chamber of the disposable flow circuit during processing, causing the heavier (greater specific gravity) components of the whole blood in the separation chamber, such as red blood cells, to move radially outwardly away from the center of rotation toward the outer or "high-G" wall of the separation chamber. The lighter (lower specific gravity) components, such as plasma, migrate toward the inner or "low-G" wall of the separation chamber. The boundary that forms between the heavier and lighter components in the separation chamber is commonly referred to as the interface. Various ones of these components can be selectively removed from the whole blood by providing appropriately located channeling structures and outlet ports in the flow circuit. For example, in one blood separation procedure, plasma is separated from cellular blood components and collected, with the cellular blood components and a replacement fluid being returned to the blood source. Alternatively, red blood cells may be harvested from the separation chamber and the rest of the blood constituents returned to the donor. Other processes are also possible including, without limitation, platelet collection, red blood cell exchanges, plasma exchanges, etc.

While many blood separation systems and procedures have employed centrifugal separation principles, there is another class of devices, based on the use of a membrane, that has been used for plasmapheresis (i.e., separating plasma from whole blood). More specifically, this type of device employs relatively rotating surfaces, at least one or which carries a porous membrane. Typically, the device employs an outer stationary housing and an internal spinning rotor covered by a porous membrane. Blood is fed into an annular space or gap between the rotor and the housing. The blood moves along the longitudinal axis of the housing toward an exit region, with plasma passing through the membrane and out of the housing into a collection bag. The remaining blood components, primarily red blood cells, platelets, and white blood cells, move to the exit region between the rotor and the housing and then are returned to the donor or conveyed into a collection bag.

A system incorporating both a centrifuge and a spinning membrane separator is described in PCT Patent Application Publication No. WO 2018/053217 A1, which is hereby incorporated by reference herein. It should be understood that blood separation may be achieved by a variety of approaches, and that centrifugation and separation via spinning membrane are merely two exemplary approaches to blood separation.

Regardless of the particular approach that is employed in separating blood into two or more constituents, the controller of the hardware must determine or be provided with the amount of blood to be processed in order to achieve a target yield for one or more target blood components. The proper amount of blood to be processed may be determined or selected by any of a number of approaches. For example, the amount of blood to be processed may be based upon the composition of the blood of the blood source, which may be determined by analyzing a blood sample from the source prior to processing. If it is not possible to analyze a blood sample, the amount of blood to be processed may be based upon an expected composition of the blood of the blood source, which may be based upon comparing characteristics of the source (e.g., sex and weight) to blood composition data taken from a larger population. The expected composition is determined experimentally from the data of the larger (but limited) population, which is intended to represent the broad masses.

It is important to accurately determine the amount of blood to be processed. If an insufficient amount of blood is processed, the target yield for the one or more target blood components will not be reached. If too much blood is processed, the procedure takes more time than is necessary, unnecessarily depletes the blood source, and may diminish the quality of the collected component (e.g., if more platelets are present in a collection bag than may be accommodated by a platelet storage solution). However, an initial estimate or determination of the amount of blood to be processed may be inaccurate for any of a number of reasons. For example, some donors (known as "dumpers") will release more platelets during the collection process than the amount that is expected. When platelets are to be collected from such a donor, more blood than necessary may be processed and more platelets than expected may be collected.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, there is provided a blood separation device. The device includes, a separator configured to receive a blood separation chamber, a pump system, and a controller. The controller is configured to determine or be provided with an initial target amount of blood to be processed in order to collect a target yield of at least one target blood component. The controller commands the pump system to convey blood from a blood source into the separator and commands the separator to separate said at least one target blood component from the blood in the separator. The controller then commands the pump system to convey said at least one target blood component out of the separator. The separation procedure continues until the initial target amount of blood to be processed has been conveyed from the blood source into the separator and said at least one target blood component separated from the initial target amount of blood to be processed has been conveyed out of the separator as an actual yield of said at least one target blood component. The initial target amount of blood to be processed is replaced with an adjusted target amount of blood to be processed based at least in part on a difference between the target yield and the actual yield when next executing the separation procedure for the same blood source.

In another aspect, there is provided a blood separation method. The method includes conveying blood from a blood source into a separator and separating at least one target blood component from the blood in the separator, with said at least one target blood component being conveyed out of the separator. The separation procedure continues until an initial target amount of blood to be processed has been conveyed from the blood source into the separator and said at least one target blood component separated from the initial target amount of blood to be processed has been conveyed out of the separator as an actual yield of said at least one target blood component. The initial target amount of blood to be processed is replaced with an adjusted target amount of blood to be processed based at least in part on a difference between a target yield of said at least one target blood component and the actual yield when next executing the separation procedure for the same blood source.

In yet another aspect, a blood processing system includes a blood separation device and a data processing system. The blood separation device includes a separator configured to receive a blood separation chamber, a pump system, and a controller configured to control the separator and the pump system to execute a blood separation procedure having a target yield of at least one target blood component using an initial target amount of blood from a blood source, with execution of the blood separation procedure resulting in an actual yield of said at least one target blood component. The data processing system is configured to access or calculate the difference between a plurality of actual yields and target yields for blood separation procedures executed for a plurality of different blood sources, select two or more of said differences, and determine an average of said two or more differences. The data processing system then determines an adjusted target amount of blood to be processed when executing the blood separation procedure for a subsequent blood source or a scaling factor to be applied when determining the adjusted target amount of blood to be processed when executing the blood separation procedure for said subsequent blood source based at least in part on said average, followed by transmitting said adjusted target amount of blood or said scaling factor to the controller when the blood separation device is to be used to execute a blood separation procedure for said subsequent blood source.

In another aspect, a blood separation method includes conveying blood from a blood source into a separator, separating at least one target blood component from the blood in the separator, conveying said at least one target blood component out of the separator, and continuing to execute the procedure until an initial target amount of blood to be processed has been conveyed from the blood source into the separator and said at least one target blood component separated from the initial target amount of blood to be processed has been conveyed out of the separator as an actual yield of said at least one target blood component. The difference between a target yield of said at least one target blood component and the actual yield is recorded. The procedure is repeated for a plurality of different blood sources, followed by determining a scaling factor based at least in part on an average of at least two of said recorded differences. The procedure is then executed for a subsequent blood source, with the initial target amount of blood to be processed being replaced with an adjusted target amount of blood to be processed based at least in part on said scaling factor.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

Figure 1:
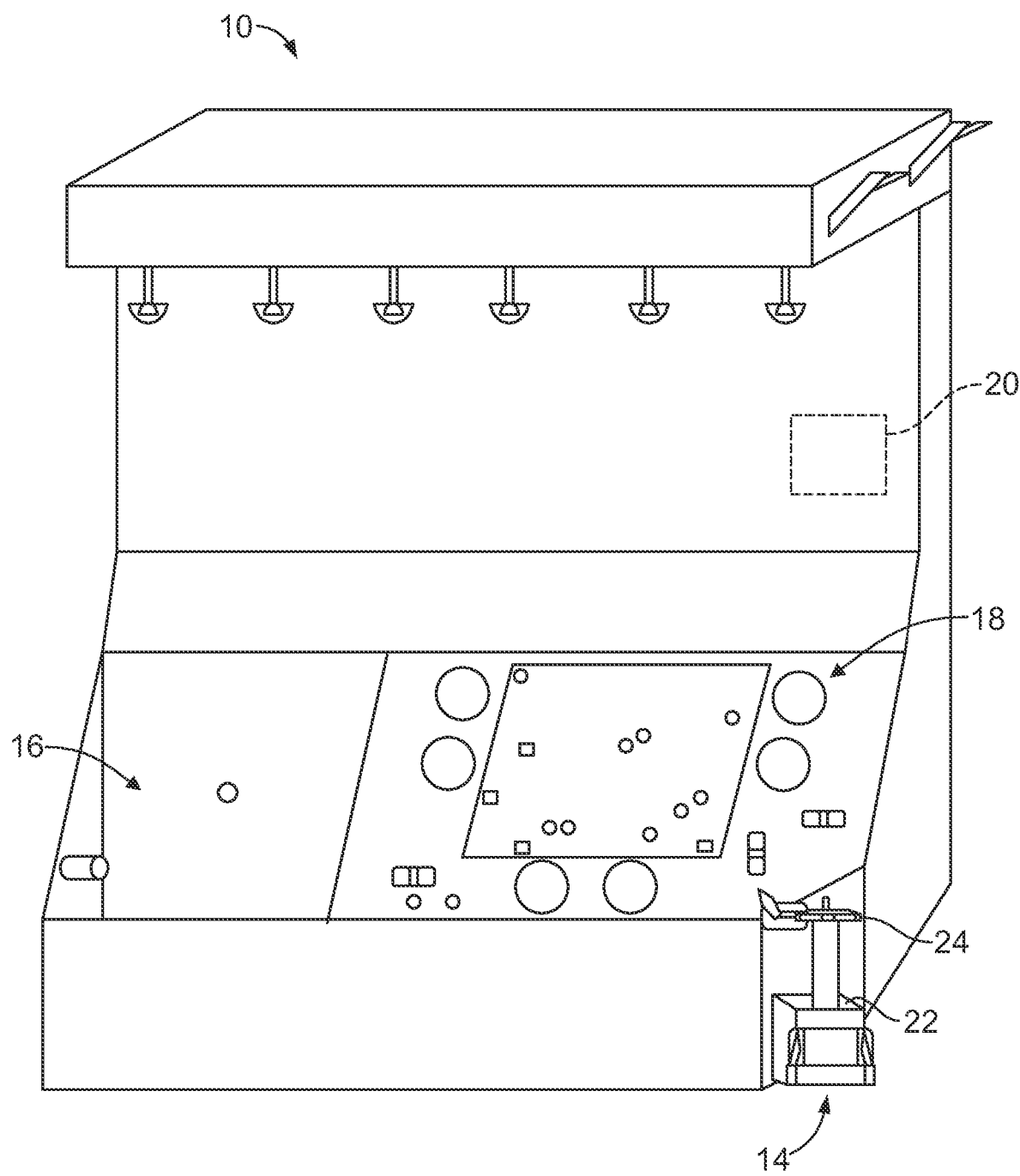
FIG. 1 is a is a perspective view of an exemplary blood separation device employing aspects of the present disclosure.
Figure 2:
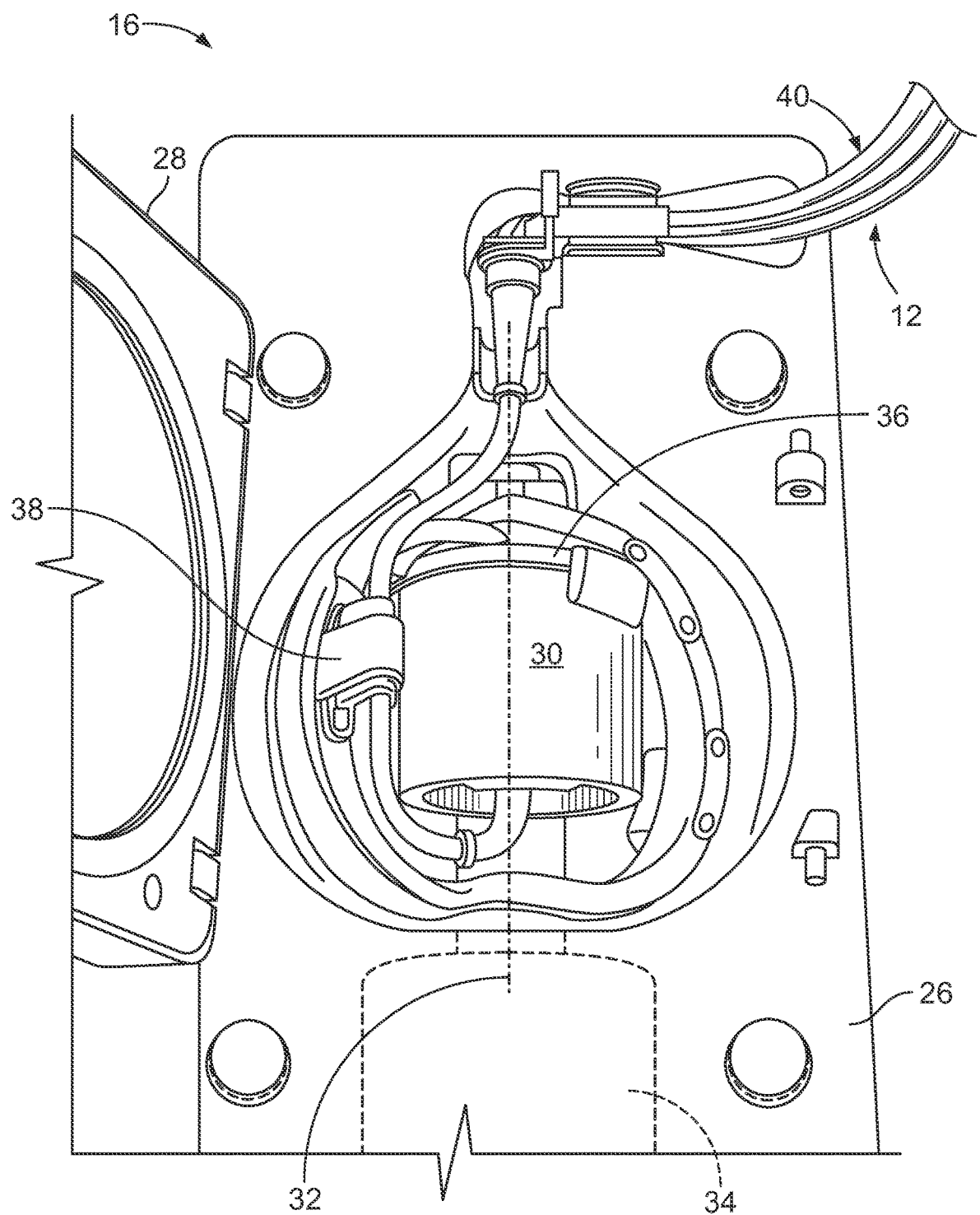
FIG. 2 is a perspective view of an exemplary centrifugal separator of the blood separation device of FIG. 1.

Systems according to the present disclosure will typically include two principal components—a durable or reusable blood separation device 10 (FIG. 1) and a disposable fluid flow circuit 12 (FIG. 2). It should be understood that the illustrated blood separation device 10 and fluid flow circuit 12 are merely exemplary and that the principles described herein may be practiced with a variety of differently configured blood separation devices and fluid flow circuits.

The illustrated blood separation device 10 includes a spinning membrane separator drive unit 14, a centrifuge or centrifugal separator 16 (FIG. 2), a pump system 18 and various valves that control fluid flow through the disposable flow circuit 12, and assorted other components (e.g., sensors, weight scales, etc.). The blood separation device 10 also includes a controller 20 that governs the operation of the other components of the blood separation device 10 to perform a blood processing and collection procedure selected by an operator. The controller 20 may be variously configured without departing from the scope of the present disclosure. In one embodiment, the controller 20 may include a microprocessor (which, in fact may include multiple physical and/or virtual processors). According to other embodiments, the controller 20 may include one or more electrical circuits designed to carry out the actions described herein. In fact, the controller 20 may include a microprocessor and other circuits or circuitry. In addition, the controller 20 may include one or more memories. The instructions by which the microprocessor is programmed may be stored on the memory associated with the microprocessor, which memory/memories may include one or more tangible non-transitory computer readable memories, having computer executable instructions stored thereon, which when executed by the microprocessor, may cause the microprocessor to carry out one or more actions as described below.

The illustrated spinning membrane separator drive unit 14 is configured to accommodate a generally cylindrical spinning membrane separator of the fluid flow circuit 12. PCT Patent Application Publication No. WO 2012/125457 A1, which is hereby incorporated by reference herein, describes an exemplary spinning membrane separator that would be suitable for incorporation into the fluid flow circuit 12, but it should be understood that the spinning membrane separator and the matching spinning membrane separator drive unit 14 may be differently configured without departing from the scope of the present disclosure.

The spinning membrane separator drive unit 14 may include a base 22 configured to receive a lower portion of the spinning membrane separator and an upper end cap 24 to receive an upper portion of the spinning membrane separator. The upper end cap 24 may be positioned directly above the base 22 to orient a spinning membrane separator received by the spinning membrane separator drive unit 14 vertically and to define a vertical axis about which the spinning membrane separator is spun. While it may be advantageous for the spinning membrane separator drive unit 14 to vertically orient a spinning membrane separator, it is also within the scope of the present disclosure for the spinning membrane separator to be differently oriented when mounted to the blood separation device 10.

At least one of the base 22 and the upper end cap 24 is configured to spin one or more components of the spinning membrane separator about the axis defined by the spinning membrane separator drive unit 14. The mechanism by which the spinning membrane separator drive unit 14 spins one or more components of the spinning membrane separator may vary without departing from the scope of the present disclosure. In one embodiment, a component of the spinning membrane separator to be spun includes at least one element configured to be acted upon by a magnet (e.g., a metallic material), while the spinning membrane separator drive unit 14 includes a magnet (e.g., a series of magnetic coils or semi-circular arcs). By modulating the magnetic field acting upon the aforementioned element of the spinning membrane separator, the component or components of the spinning membrane separator may be made to spin in different directions and at varying speeds. In other embodiments, different mechanisms may be employed to spin the component or components of the spinning membrane separator.

Regardless of the mechanism by which the spinning membrane separator drive unit 14 spins the component or components of the spinning membrane separator, the component or components of the spinning membrane separator is/are preferably spun at a speed that is sufficient to create Taylor vortices in a gap between the spinning component and a stationary component of the spinning membrane separator (or a component that spins at a different speed). Fluid to be separated within the spinning membrane separator flows through this gap, and filtration may be dramatically improved by the creation of Taylor vortices.

Typically, a spinning membrane separator drive unit 14 and matching spinning membrane separator are used to separate plasma from cellular blood components. For example, in one embodiment blood enters a gap between an outer stationary housing and an internal spinning rotor covered by a porous membrane. The blood moves along the longitudinal axis of the housing toward an exit region, with plasma passing through the membrane and out of the housing into a collection bag. The remaining blood components, primarily red blood cells, platelets, and white blood cells, move to the exit region between the rotor and the housing and then are returned to the donor or conveyed into a collection bag. While it is most common for a spinning membrane separator drive unit 14 and matching spinning membrane separator to be used to separate plasma from other blood components, it is within the scope of the present disclosure for the combination (if provided) to separate other blood components.

As for the centrifugal separator 16, it includes a centrifuge compartment 26 that may receive the other components of the centrifugal separator 16 (FIG. 2). The centrifuge compartment 26 may include a lid 28 that is opened to insert and remove a centrifugal separation chamber 30 of the fluid flow circuit 12. During a separation procedure, the lid 28 may be closed with the centrifugal separation chamber 30 positioned within the centrifuge compartment 26, as the centrifugal separation chamber 30 is spun or rotated about an axis 32 under the power of an electric drive motor or rotor 34 of the centrifugal separator 16.

The illustrated centrifugal separator 16 includes a carriage or support 36 that holds the centrifugal separation chamber 30 and a yoke member 38. The yoke member 38 engages an umbilicus 40 of the fluid flow circuit 12, which extends between the centrifugal separation chamber 30 and one or more other components (e.g., a cassette) of the fluid flow circuit 12. The yoke member 38 causes the umbilicus 40 to orbit around the centrifugal separation chamber 30 at a one omega rotational speed. The umbilicus 40 twists about its own axis as it orbits around the centrifugal separation chamber 30. The twisting of the umbilicus 40 about its axis as it rotates at one omega with the yoke member 38 imparts a two omega rotation to the centrifugal separation chamber 30, according to known design. The relative rotation of the yoke member 38 at a one omega rotational speed and the centrifugal separation chamber 30 at a two omega rotational speed keeps the umbilicus 40 untwisted, avoiding the need for rotating seals.

Blood is introduced into the centrifugal separation chamber 30 by the umbilicus 40, with the blood being separated (e.g., into a layer of less dense components, such as platelet-rich plasma, and a layer of more dense components, such as packed red blood cells) within the centrifugal separation chamber 30 as a result of centrifugal forces as it rotates. Components of an interface monitoring system may be positioned within the centrifuge compartment 26 to oversee separation of blood within the centrifugal separation chamber 30, with the controller 20 adjusting operation of the various components of the blood separation device 10 in response to transmissions from the interface monitoring system. For example, the controller 20 may command the pump system 18 to operate differently in order to adjust the position of an interface between separated blood components within the centrifugal separation chamber 30.

The separated blood components are conveyed out of the centrifugal separation chamber 30 for collection or return to the blood source. If additional processing of one of the components is required, then it may be conveyed into a second separator (e.g., the spinning membrane separator drive unit 14) or back into the centrifugal separator 16. For example, if platelets are to be collected, the blood may be separated in a first compartment of the centrifugal separation chamber 30 into packed red blood cells and platelet-rich plasma. The packed red blood cells are conveyed out of the centrifugal separation chamber 30 for collection or return to the blood source, while the platelet-rich plasma is conveyed out of the first compartment of the centrifugal separation chamber 30 and into a second compartment of the centrifugal separation chamber 30. The platelet-rich plasma in the second compartment separates into platelet-poor plasma and platelet concentrate, with the plasma being conveyed out of the centrifugal separation chamber 30 while platelet concentrate remains in the second compartment. The platelet concentrate may remain in the second compartment of the centrifugal separation chamber 30 at the end of the procedure as a collected product or may be conveyed out of the second compartment for collection in a separate container.

While the illustrated blood separation device 10 includes two separators, it should be understood that a blood separation device according to the present disclosure may have only one separator (e.g., only a centrifugal separator or only a spinning membrane separator drive unit or a differently configured separator). If two separators are provided, as in the illustrated embodiment, blood may be separated using only one of the separators or both separators. For example, if the centrifugal separation chamber 30 includes only one compartment, blood may be conveyed into the centrifugal separator 16, which separates the blood into two or more components (e.g., red blood cells and platelet-rich plasma). One of the components may be conveyed from the centrifugal separator 16 into the spinning membrane separator drive unit 14, where it is further separated (e.g., into platelet-poor plasma and platelet concentrate) or processed.

Regardless of the particular configuration of the blood separation device 10, the separator(s), and the controller 20, the controller 20 is configured and/or programmed to execute at least one blood processing application but, more advantageously, is configured and/or programmed to execute a variety of different blood processing applications. In any of these procedures, it is important that the proper amount of blood is drawn from the blood source in order to achieve the goals of the procedure (e.g., collecting a particular volume of a blood component). In view of the possibility of there being a difference between an initial target amount of blood to be processed in order to achieve the goals of the procedure and the proper amount of blood that should have been processed, the controller 20 is configured or programmed to assess the difference and generate an adjusted target amount of blood to be processed (or to be provided with an adjusted target amount of blood to be processed) during a subsequent procedure.

For example, in an exemplary procedure, the blood separation device 10 is used to collect platelets from a blood source. It should be understood that the following procedure is merely exemplary and that the principles described herein may be employed in collecting other blood components (e.g., red blood cells, mononuclear cells, or plasma).

In an exemplary platelet collection or depletion procedure, the controller 20 determines or is provided with an initial target amount of blood to be processed in order to collect a target yield of platelets. The initial target amount of blood to be processed may be based on any suitable data and may be determined or selected based on any suitable approach. For example, US Patent Application Publication No. 2017/0354770 (which is hereby incorporated by reference herein) provides the following formula for calculating an initial target amount of blood to be processed:

$$WB_{total\ processed\ (+AC)}(\text{mL}) = -\ln\left(\frac{Plt_{post}}{Plt_{pre}}\right) \times \frac{TBV}{CE}, \quad (1)$$

where
 $Plt_{post}$ is a selected platelet post-count,
 $Plt_{pre}$ is a measured platelet pre-count,
 TBV is the total blood volume of the blood source, and
 CE is the platelet collection efficiency of the blood separation device 10.

The controller 20 commands the pump system 18 to convey blood from a blood source into one of the separators 14, 16, with anticoagulant optionally being added to the blood prior to the blood entering the separator 14, 16. The controller 20 commands the separator 14, 16 (or separators 14 and 16, if both separators 14 and 16 are required to isolate the at least one target blood component) to separate the at least one target blood component (platelets, in this example) from the blood, as described above. The controller 20 commands the pump system 18 to convey the target blood component out of the separator 14, 16 and to the appropriate destination, which may be a collection container, for example.

The controller 20 continues commanding the various components of the blood separation device 10 to draw blood from the blood source and isolate the target blood component until the initial target amount of blood to be processed has been conveyed from the blood source into the separator 14, 16 and separated. The amount of the target blood component isolated at the end of the procedure may be referred to as the actual yield of the target blood component (which is platelets in this example). The actual yield may be determined by any suitable approach, which may depend upon the nature of the target blood component. For example, if the target blood component is a cellular blood component, a cell counter may be used in determining the actual yield.

On the other hand, if the target component is plasma, a weight scale may be used to determine the actual yield.

The difference between the actual yield of the target blood component and the target yield is then determined. The difference may be expressed in any appropriate units, which may include the number of blood cells or a volume or weight of a targeted substance, or may be unit-less. In one embodiment, the difference is presented as a percentage or a ratio. Thus, if the actual yield is 10% greater than the target yield, then the difference may be presented as 10% or 110% or as a 1.1:1 ratio. The difference may be determined by the controller 20 or by some other entity, such as a central computer or data management system or data processing system that calculates and stores the differences for blood separation procedures carried out by all of the blood separation devices at a facility or within a network of facilities.

The difference between the actual yield of the target blood component and the target yield is used to determine an adjusted target amount of blood to be processed. For example, if it is determined that more blood was processed than was necessary (i.e., if the initial target amount of blood to be processed was too high), then the adjusted target amount of blood to be processed will be lower than the initial target amount of blood to be processed. On the other hand, if it is determined that less blood was processed than should have been (i.e., if the initial target amount of blood to be processed was too low), then the adjusted target amount of blood to be processed will be higher than the initial target amount of blood to be processed. The adjusted target amount of blood to be processed may be determined by the controller 20 (either after the controller 20 has determined the difference between the target and actual yields or after the controller 20 has been provided with the difference between the target and actual yields) or by some other entity, such as the aforementioned central computer or data management system or data processing system.

The adjusted target amount of blood to be processed may be determined by any suitable approach, which may include an approach that is similar to the one taken to determine the initial target amount of blood to be processed. In one embodiment, the formula for determining the adjusted target amount of blood to be processed may be identical to the formula used to determine the initial target amount of blood to be processed (e.g., above formula (1)) except for the inclusion of a scaling factor based at least in part on the difference between the target and actual yields. For example, the scaling factor may be a multiplier that is correlated to the difference between the target and actual yields. Thus, if the difference between the target and actual yields indicates that the target yield could have been collected using 10% less blood, then the scaling factor may be 0.9, which results in an adjusted target amount of blood to be processed that is 10% less than the initial target amount of blood to be processed. Similarly, if the difference between the target and actual yields indicates that 10% more blood should have been processed in order to collect the target yield of the targeted blood component, then the scaling factor may be 1.1, which results in an adjusted target amount of blood to be processed that is 10% greater than the initial target amount of blood to be processed. According to another exemplary approach, the scaling factor may be equivalent to the amount of blood to process to account for the difference between the target and actual yields, with the scaling factor being added to or subtracted from the initial target amount of blood to be processed, as appropriate. It should again be emphasized that these approaches are merely exemplary, and that other approaches may be employed without departing from the scope of the present disclosure.

Regardless of whether the controller 20 determines the adjusted target amount of blood to be processed or is provided with the adjusted target amount of blood to be processed, the controller 20 replaces the initial target amount of blood to be processed with the adjusted target amount of blood to be processed when next executing the same procedure for the same blood source. Thus, the next time that the blood source is subjected to the same procedure (either using the same blood separation device 20 or a different one that has been provided with the adjusted target amount of blood to be processed), the procedure will be identical to the first time that the procedure was executed, except that a different amount of blood (corresponding to the adjusted target amount of blood to be processed) will be used. If, following this second iteration of the same procedure, it is determined that there is still a difference between the target yield and the actual yield (using the adjusted target amount of blood to be processed), a further adjusted target amount of blood to be processed may be determined according to the above-described approach to determining the adjusted target amount of blood to be processed. The further adjusted target amount of blood to be processed is used for a third iteration of the same procedure. This process of executing a separation procedure and formulating a new target amount of blood to be processed during a successive procedure may be repeated to continue improving the estimate for the proper amount of blood to be processed. This may be especially advantageous for repeat patient-types of procedures, such as therapeutic plasma exchange, red blood cell collection, and mononuclear cell collection.

It should be understood that the adjusted target amount of blood to be processed may include other factors, including being based at least in part on the difference between target and actual yields for another blood source. Indeed, a broader data set for determining an adjusted target amount of blood could include the differences between target and actual yields for all of the blood sources within a facility or center or region or may include all blood sources. Thus, the adjusted target amount of blood to be processed may be personal to the blood source, along with being used in improving the separation algorithms for other blood sources. If data from multiple different sources is used, the sources may be grouped by any suitable categorization(s), such as: sex, height, weight, ethnicity, hematocrit, pre-count of a cellular component of interest (e.g., a platelet pre-count), protein counts, etc. Machine learning techniques may be employed to determine the one or more factors that are most appropriate for grouping the data of multiple sources when correlating target and actual yields.

An adjusted target amount of blood to be processed may also be based on a difference between at least one blood source characteristic before and after executing a separation procedure. Examples of possible characteristics to be factored into the adjusted target amount of blood to be processed include pre- and post-procedure hematocrit (which is used to determine the rate at which the kidneys remove the crystalloid volume introduced during the procedure) and platelet count (i.e., platelet pre-count vs. platelet post-count). Machine learning techniques may be used, in combination with pre- and post-procedure blood source characteristics, to further improve the separation algorithms.

Furthermore, an adjusted target amount of blood to be processed may be based on multiple differences between target and actual yields for the same blood source. For example, if the same procedure has been executed three times for the same blood source, with the difference between target and actual yields having been determined three times, all three of the difference values (or at least two of the difference values) may be used in calculating a new adjusted target amount of blood to be processed for the next time that the blood source is subjected to the procedure. According to an exemplary approach, a moving average approach may be employed, which may include different values being equally or differently weighted when calculating an adjusted target amount of blood to be processed.

Indeed, on account of there inherently being some form of random variation in the collection of the data to be used in any of the preceding analyses, any of a number of statistical techniques may be employed to reduce the effects of these random variations. For any of these techniques, the goal is to arrive at the approach resulting in the smallest mean squared error. As noted above, two such techniques are to take the average or mean of all past observations (for either a single source or multiple sources), with all past observations being weighted equally, or to employ a moving average.

A moving average computes the mean of successive smaller sets of numbers of past data and gives more importance or weight to more recent data. The number of the observations can vary, with machine learning techniques optionally being used to determine the optimal number of observations to be used to produce the smallest mean squared error. For example, the following is an equation for a simple moving average:

$$\hat{y}_t = \frac{1}{k}\sum_{n=0}^{k-1} y_{t-n}, \quad (2)$$

in which
$\hat{y}_t$ the moving average for t,
t is total number of observations,
k is the number of observations being used in the calculation, and
$y_{t-n}$ is value of the observation at t−n. Thus, if there are thirty observations that have been made (t=30) and only the most recent three observations are being used in the calculation (k=3), the equation will calculate the sum of the three most recent values ($y_{30}$ or $y_{t-0}$, $y_{29}$ or $y_{t-1}$, and $y_{28}$ or $y_{t-2}$) and divide the sum by three to arrive at the moving average.

Machine learning techniques may be applied to determine the optimal k value by calculating the moving average for different k values. For each k value, the mean squared error is calculated, followed by the mean squared error values being compared to determine which k value produces the smallest mean squared error. The moving average calculated using that k value may then be selected as the calculated average (of the difference between target and actual yields) for determining an adjusted target amount of blood to be processed and/or a scaling factor to be applied when calculating an adjusted target amount of blood to be processed.

Another technique, which is known as double moving averages for a linear trend process, can also be used. Such an approach entails calculating a second moving average from the original moving average, using the same value for k. As soon as both single and double moving averages are available, a computer routine uses these averages to compute a slope and intercept, and then forecasts one or more periods ahead. Again, machine learning techniques may be used, with the optimal k value being determined by solving for the value of k resulting in the smallest mean squared error and then using the moving average calculated using that k value as the calculated average for determining an adjusted target amount of blood to be processed and/or a scaling factor to be applied when calculating an adjusted target amount of blood to be processed.

Another technique is known as exponential smoothing, which assigns exponentially decreasing weights as the observation get older. In other words, recent observations are given relatively more weight in forecasting than the older observations. In the case of moving averages, the weights assigned to the observations included in the calculation are the same. In exponential smoothing, however, there are one or more smoothing parameters to be determined (or estimated) and these choices determine the weights assigned to the observations included in the calculation. In an exemplary embodiment, this smoothing scheme employs the following equation:

$$S_t = \alpha y_{t-1} + (1-\alpha)S_{t-1}, \quad (3)$$
$$0 < \alpha \le 1,$$
$$t \ge 3.$$

This approach begins by setting $S_2$ to $y_1$, where $S_i$ stands for smoothed observation and y stands for the original observation. The subscripts refer to the time periods, 1, 2, ..., n. For the third period, $S_3=\alpha^*y_2+(1-\alpha)^*S_2$; and so on. There is no $S_1$, but rather the smoothed series starts with the smoothed version of the second observation. The speed at which the older responses are dampened (smoothed) is a function of the value of $\alpha$. When $\alpha$ is close to 1, dampening is quick, and when $\alpha$ is close to 0, dampening is slow. Machine learning techniques can be used to find the best value for $\alpha$ which results in the smallest mean squared error. The smoothed value calculated using that $\alpha$ value is then used as the calculated average for determining an adjusted target amount of blood to be processed and/or a scaling factor to be applied when calculating an adjusted target amount of blood to be processed.

In addition to exponential smoothing methods, double or triple (Holt-Winters methods) exponential smoothing methods, in which two or three constants are used to better handle trends, may also be used.

Below are two equations associated with double exponential smoothing:

$$S_t = \alpha y_t + (1-\alpha)(S_{t-1} + b_{t-1}) \quad 0 \le \alpha \le 1 \quad (4)$$
$$b_t = \gamma(S_t - S_{t-1}) + (1-\gamma)b_{t-1} \quad 0 \le \gamma \le 1 \quad (5)$$

Notably, the current value of the series is used to calculate its smoothed value replacement in double exponential smoothing. As for the values for $\alpha$ and $\gamma$, they can be obtained via non-linear optimization techniques, such as the Marquardt Algorithm. As with the above-described exponential smoothing technique, once optimal values are determined using machine learning techniques, the smoothed value produced by the $\alpha$ and $\gamma$ values resulting in the smallest mean squared error may be used as the calculated average for determining an adjusted target amount of blood to be processed and/or a scaling factor to be applied when calculating an adjusted target amount of blood to be processed.

As for triple exponential smoothing, the following equations may be employed, in one embodiment:

$$S_t = \alpha \frac{y_t}{I_{t-L}} + (1-\alpha)(S_{t-1} + b_{t-1}) \quad (6)$$

for overall smoothing, $$b_t = \gamma(S_t - S_{t-1}) + (1-\gamma)b_{t-1} \quad (7)$$

for trend smoothing, $$I_t = \beta \frac{y_t}{S_t} + (1-\beta)I_{t-L} \quad (8)$$

for seasonal smoothing, and $$F_{t+m} = (S_t + mb_t)I_{t-L+m} \quad (9)$$

for forecasting, in which
y is the observation,
S is the smoothed observation,
b is the trend factor,
I is the seasonal index,
F is the forecast at m periods ahead, and
t is an index denoting a time period.

In accordance with the preceding descriptions of exponential smoothing and double exponential smoothing, machine learning techniques may be used to determine the α, β, and γ values resulting in the smallest mean squared error. Once these values have been determined, the resulting smoothed observation may be selected as the calculated average for determining an adjusted target amount of blood to be processed and/or a scaling factor to be applied when calculating an adjusted target amount of blood to be processed. Again, it should be understood that the foregoing approaches are merely exemplary techniques that may be employed when deriving the adjusted target amount of blood to be processed and/or a scaling factor to be used to calculate the adjusted target amount of blood to be processed from data sets including multiple recorded differences between target and actual yields for a single blood source or for a plurality of different blood sources.

Aspects

Aspect 1. A blood separation device, comprising: a separator configured to receive a blood separation chamber; a pump system; and a controller configured to (a) determine or be provided with an initial target amount of blood to be processed in order to collect a target yield of at least one target blood component, (b) command the pump system to convey blood from a blood source into the separator, (c) command the separator to separate said at least one target blood component from the blood in the separator, (d) command the pump system to convey said at least one target blood component out of the separator, (e) continue executing (b)-(d) until the initial target amount of blood to be processed has been conveyed from the blood source into the separator and said at least one target blood component separated from the initial target amount of blood to be processed has been conveyed out of the separator as an actual yield of said at least one target blood component, and (f) replace the initial target amount of blood to be processed with an adjusted target amount of blood to be processed based at least in part on a difference between the target yield and the actual yield when next executing (b)-(e) for the same blood source.

Aspect 2. The blood separation device of Aspect 1, wherein the controller is configured to replace the adjusted target amount of blood to be processed with a further adjusted target amount of blood to be processed based at least in part on a difference between the target yield and the actual yield after executing (b)-(e) using the adjusted target amount of blood to be processed.

Aspect 3. The blood separation device of any one of the preceding Aspects, wherein the controller is configured to determine the difference between the target yield and the actual yield, and determine the adjusted target amount of blood to be processed.

Aspect 4. The blood separation device of any one of Aspects 1-2, wherein the controller is configured to be provided with the difference between the target yield and the actual yield and to determine the adjusted target amount of blood to be processed.

Aspect 5. The blood separation device of any one of Aspects 1-2, wherein the controller is configured to be provided with a scaling factor based at least in part on the difference between the target yield and the actual yield and to determine the adjusted target amount of blood to be processed based at least in part on said scaling factor.

Aspect 6. The blood separation device of any one of Aspects 1-2, wherein the controller is configured to be provided with the adjusted target amount of blood to be processed.

Aspect 7. The blood separation device of any one of the preceding Aspects, wherein the adjusted target amount of blood to be processed is based at least in part on a difference between at least one blood source characteristic before and after executing (b)-(e).

Aspect 8. The blood separation device of any one of the preceding Aspects, wherein the controller is configured to access a plurality of recorded differences between target and actual yields for the blood source, determine an average of two or more of said plurality of recorded differences, and determine the adjusted target amount of blood to be processed based at least in part on said average.

Aspect 9. The blood separation device of Aspect 8, wherein controller is configured to weigh at least two of said two or more recorded differences differently when determining said average.

Aspect 10. The blood separation device of Aspect 9, wherein the controller is configured to employ exponential smoothing techniques when determining the weight to be assigned to at least one of said recorded differences.

Aspect 11. The blood separation device of Aspect 8, wherein the controller is configured to calculate at least one moving average when determining the adjusted target amount of blood to be processed.

Aspect 12. The blood separation device of any one of Aspects 8-11, wherein the controller is configured to employ machine learning techniques to determine the number of recorded differences to be included when determining said average so as to produce the smallest mean squared error when determining said average.

Aspect 13. A blood separation method, comprising: (a) conveying blood from a blood source into a separator, (b) separating at least one target blood component from the blood in the separator, (c) conveying said at least one target blood component out of the separator, (d) continuing to execute (a)-(c) until an initial target amount of blood to be processed has been conveyed from the blood source into the separator and said at least one target blood component separated from the initial target amount of blood to be processed has been conveyed out of the separator as an actual yield of said at least one target blood component, and (e) replacing the initial target amount of blood to be processed with an adjusted target amount of blood to be processed based at least in part on a difference between a target yield of said at least one target blood component and the actual yield when next executing (a)-(d) for the same blood source.

Aspect 14. The blood separation method of Aspect 13, further comprising replacing the adjusted target amount of blood to be processed with a further adjusted target amount of blood to be processed based at least in part on a difference between the target yield and the actual yield after executing (a)-(d) using the adjusted target amount of blood to be processed.

Aspect 15. The blood separation method of any one of Aspects 13-14, wherein the adjusted target amount of blood to be processed is based at least in part on a difference between at least one blood source characteristic before and after executing (a)-(d).

Aspect 16. The blood separation method of any one of Aspects 13-15, further comprising executing (a)-(d) a plurality of times, recording the difference between the target and actual yields each time that (a)-(d) is executed, selecting two or more of said recorded differences, determining an average of said two or more recorded differences, and determining the adjusted target amount of blood to be processed based at least in part on said average.

Aspect 17. The blood separation method of Aspect 16, wherein at least two of said two or more recorded differences are weighted differently when determining said average.

Aspect 18. The blood separation method of Aspect 17, wherein the weight to be assigned to at least one of said recorded differences is determined using exponential smoothing techniques.

Aspect 19. The blood separation method of Aspect 16, wherein said determining the adjusted target amount of blood to be processed includes calculating at least one moving average.

Aspect 20. The blood separation method of any one of Aspects 16-19, wherein said selecting two or more of said recorded differences includes employing machine learning techniques to determine the number of recorded differences to be selected so as to produce the smallest mean squared error when determining said average.

Aspect 21. A blood processing system, comprising: a blood separation device including a separator configured to receive a blood separation chamber, a pump system, and a controller configured to control the separator and the pump system to execute a blood separation procedure having a target yield of at least one target blood component using an initial target amount of blood from a blood source, with execution of the blood separation procedure resulting in an actual yield of said at least one target blood component; and a data processing system configured to communicate with the controller, wherein the data processing system is configured to access or calculate the difference between a plurality of actual yields and target yields for blood separation procedures executed for a plurality of different blood sources, select two or more of said differences, determine an average of said two or more differences, determine an adjusted target amount of blood to be processed when executing the blood separation procedure for a subsequent blood source or a scaling factor to be applied when determining the adjusted target amount of blood to be processed when executing the blood separation procedure for said subsequent blood source based at least in part on said average, and transmit said adjusted target amount of blood or said scaling factor to the controller when the blood separation device is to be used to execute a blood separation procedure for said subsequent blood source.

Aspect 22. The blood processing system of Aspect 21, wherein the data processing system is configured to select said two or more differences based on a similarity between at least one of the sex, height, weight, ethnicity, hematocrit, pre-count of a cellular component of interest, and protein count among the plurality of different blood sources.

Aspect 23. The blood processing system of any one of Aspects 21-22, wherein the data processing system is configured to apply the same weight to each one of said two or more differences when determining said average.

Aspect 24. The blood processing system of any one of Aspects 21-22, wherein the data processing system is configured to apply different weights to at least two of said two or more differences when determining said average.

Aspect 25. The blood processing system of Aspect 24, wherein the weight to be assigned to at least one of said differences is determined by the data processing system using exponential smoothing techniques.

Aspect 26. The blood processing system of Aspect 24, wherein the weight to be assigned to at least one of said differences is determined by the data processing system using double exponential smoothing techniques.

Aspect 27. The blood processing system of Aspect 24, wherein the weight to be assigned to at least one of said differences is determined by the data processing system using triple exponential smoothing techniques.

Aspect 28. The blood processing system of Aspect 24, wherein the data processing system is configured to calculate a moving average when determining said average.

Aspect 29. The blood processing system of Aspect 28, wherein the data processing system is configured to calculate a second moving average from the moving average when determining said average.

Aspect 30. The blood processing system of any one of Aspects 21-29, wherein the data processing system is configured to employ machine learning techniques when selecting said two or more differences to determine the number of differences to be selected so as to produce the smallest mean squared error when determining said average.

Aspect 31. A blood separation method, comprising: (a) conveying blood from a blood source into a separator, (b) separating at least one target blood component from the blood in the separator, (c) conveying said at least one target blood component out of the separator, (d) continuing to execute (a)-(c) until an initial target amount of blood to be processed has been conveyed from the blood source into the separator and said at least one target blood component separated from the initial target amount of blood to be processed has been conveyed out of the separator as an actual yield of said at least one target blood component, (e) recording a difference between a target yield of said at least one target blood component and the actual yield, (f) repeating (a)-(e) for a plurality of different blood sources, (g) determining a scaling factor based at least in part on an average of at least two of said recorded differences, and (h) executing (a)-(d) for a subsequent blood source, with the initial target amount of blood to be processed being replaced with an adjusted target amount of blood to be processed based at least in part on said scaling factor.

Aspect 32. The blood separation method of Aspect 31, wherein said two or more recorded differences are selected based on a similarity between at least one of the sex, height, weight, ethnicity, hematocrit, pre-count of a cellular component of interest, and protein count among the plurality of different blood sources.

Aspect 33. The blood separation method of any one of Aspects 31-32, wherein the same weight is applied to each one of said two or more differences when determining said average.

Aspect 34. The blood separation method of any one of Aspects 31-32, wherein different weights are applied to at least two of said two or more differences when determining said average.

Aspect 35. The blood separation method of Aspect 34, wherein the weight to be assigned to at least one of said recorded differences is determined using exponential smoothing techniques.

Aspect 36. The blood separation method of Aspect 34, wherein the weight to be assigned to at least one of said recorded differences is determined using double exponential smoothing techniques.

Aspect 37. The blood separation method of Aspect 34, wherein the weight to be assigned to at least one of said recorded differences is determined using triple exponential smoothing techniques.

Aspect 38. The blood separation method of Aspect 34, wherein a moving average is calculated when determining said average.

Aspect 39. The blood separation method of Aspect 38, wherein a second moving average is calculated from the moving average when determining said average.

Aspect 40. The blood separation method of any one of Aspects 31-39, wherein machine learning techniques are employed when selecting said two or more recorded differences to determine the number of recorded differences to be selected so as to produce the smallest mean squared error when determining said average.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A blood processing system, comprising:
a blood separation device including
a separator configured to receive a blood separation chamber,
a pump system, and
a controller configured to control the separator and the pump system to execute a blood separation procedure having a target yield of at least one target blood component using an initial target amount of blood from a blood source, with execution of the blood separation procedure resulting in an actual yield of said at least one target blood component; and
a data processing system configured to communicate with the controller, wherein
the data processing system is configured to
access or calculate the difference between a plurality of actual yields and target yields for blood separation procedures executed for a plurality of different blood sources,
select two or more of said differences,
determine an average of said two or more differences,
determine an adjusted target amount of blood to be processed when executing the blood separation procedure for a subsequent blood source or a scaling factor to be applied when determining the adjusted target amount of blood to be processed when executing the blood separation procedure for said subsequent blood source based at least in part on said average, and
transmit said adjusted target amount of blood or said scaling factor to the controller when the blood separation device is to be used to execute a blood separation procedure for said subsequent blood source and the controller is further configured to control the separator and the pump system to execute said blood separation procedure for said subsequent blood source, with the initial target amount of blood being replaced with said adjusted target amount of blood.

2. The blood processing system of claim 1, wherein the data processing system is configured to select said two or more differences based on a similarity between at least one of the sex, height, weight, ethnicity, hematocrit, pre-count of a cellular component of interest, and protein count among the plurality of different blood sources.

3. The blood processing system of claim 1, wherein the data processing system is configured to apply the same weight to each one of said two or more differences when determining said average.

4. The blood processing system of claim 1, wherein the data processing system is configured to apply different weights to at least two of said two or more differences when determining said average.

5. The blood processing system of claim 4, wherein the weight to be assigned to at least one of said differences is determined by the data processing system using exponential smoothing techniques.

6. The blood processing system of claim 4, wherein the weight to be assigned to at least one of said differences is determined by the data processing system using double exponential smoothing techniques.

7. The blood processing system of claim 4, wherein the weight to be assigned to at least one of said differences is determined by the data processing system using triple exponential smoothing techniques.

8. The blood processing system of claim 4, wherein the data processing system is configured to calculate a moving average when determining said average.

9. The blood processing system of claim 8, wherein the data processing system is configured to calculate a second moving average from the moving average when determining said average.

10. The blood processing system of claim 1, wherein the data processing system is configured to employ machine learning techniques when selecting said two or more differences to determine the number of differences to be selected so as to produce the smallest mean squared error when determining said average.

11. A blood separation method, comprising:
(a) conveying blood from a blood source into a separator,
(b) separating at least one target blood component from the blood in the separator,
(c) conveying said at least one target blood component out of the separator, (d) continuing to execute (a)-(c) until an initial target amount of blood to be processed has been conveyed from the blood source into the separator and said at least one target blood component separated from the initial target amount of blood to be processed has been conveyed out of the separator as an actual yield of said at least one target blood component, (e) recording a difference between a target yield of said at least one target blood component and the actual yield, (f) repeating (a)-(e) for a plurality of different blood sources, (g) determining a scaling factor based at least in part on an average of at least two of said recorded differences, and (h) executing (a)-(d) for a subsequent blood source, with the initial target amount of blood to be processed being replaced with an adjusted target amount of blood to be processed based at least in part on said scaling factor.

12. The blood separation method of claim 11, wherein said two or more recorded differences are selected based on a similarity between at least one of the sex, height, weight, ethnicity, hematocrit, pre-count of a cellular component of interest, and protein count among the plurality of different blood sources.

13. The blood separation method of claim 11, wherein the same weight is applied to each one of said two or more differences when determining said average.

14. The blood separation method of claim 11, wherein different weights are applied to at least two of said two or more differences when determining said average.

15. The blood separation method of claim 14, wherein the weight to be assigned to at least one of said recorded differences is determined using exponential smoothing techniques.

16. The blood separation method of claim 14, wherein the weight to be assigned to at least one of said recorded differences is determined using double exponential smoothing techniques.

17. The blood separation method of claim 14, wherein the weight to be assigned to at least one of said recorded differences is determined using triple exponential smoothing techniques.

18. The blood separation method of claim 14, wherein a moving average is calculated when determining said average.

19. The blood separation method of claim 18, wherein a second moving average is calculated from the moving average when determining said average.

20. The blood separation method of claim 11, wherein machine learning techniques are employed when selecting said two or more recorded differences to determine the number of recorded differences to be selected so as to produce the smallest mean squared error when determining said average.

* * * * *